US011439607B2

(12) United States Patent
Staal et al.

(10) Patent No.: US 11,439,607 B2
(45) Date of Patent: Sep. 13, 2022

(54) USE OF SENICAPOC FOR TREATMENT OF NEUROPATHIC PAIN

(71) Applicant: Paracelsus Neuroscience I, LLC, Metuchen, NJ (US)

(72) Inventors: Roland Staal, Metuchen, NJ (US); Thomas Möller, Brookline, MA (US)

(73) Assignee: Paracelsus Neuroscience I, LLC, Metuchen, NJ (US)

( * ) Notice: Subject to any disclaimer, the term of this patent is extended or adjusted under 35 U.S.C. 154(b) by 33 days.

(21) Appl. No.: 16/344,645

(22) PCT Filed: Oct. 23, 2017

(86) PCT No.: PCT/US2017/057930
§ 371 (c)(1),
(2) Date: Apr. 24, 2019

(87) PCT Pub. No.: WO2018/081018
PCT Pub. Date: May 3, 2018

(65) Prior Publication Data
US 2020/0046657 A1 Feb. 13, 2020

Related U.S. Application Data

(60) Provisional application No. 62/412,580, filed on Oct. 25, 2016.

(51) Int. Cl.
*A61K 31/165* (2006.01)
*A61P 29/02* (2006.01)

(52) U.S. Cl.
CPC ............ *A61K 31/165* (2013.01); *A61P 29/02* (2018.01)

(58) Field of Classification Search
CPC .................................................. A61K 31/165
See application file for complete search history.

(56) References Cited

U.S. PATENT DOCUMENTS

| | | | | |
|---|---|---|---|---|
| 6,288,122 B1* | 9/2001 | McNaughton-Smith | ................... | A61K 31/165 514/617 |
| 8,455,549 B2* | 6/2013 | Madsen | ................... | A61P 19/02 514/617 |
| 2004/0229803 A1* | 11/2004 | Stephenson | ............ | A61K 31/34 514/183 |
| 2006/0019968 A1* | 1/2006 | Baeyens Cabrera | ... | A61P 25/00 514/259.41 |
| 2006/0019969 A1* | 1/2006 | Baeyens Cabrera | ....................... | A61K 31/519 514/259.41 |
| 2010/0019968 A1* | 1/2010 | Shingyoji | ............... | G01S 19/34 342/357.48 |
| 2010/0056637 A1 | 3/2010 | Castle | | |

OTHER PUBLICATIONS

Inflammatory Disorders Definition, [online], Hospital for Special Surgery, 2010 [retrieved Jan. 21, 2021] from: https://www.hss.edu/condition-list_inflammatory-disorders.asp.*
Reagan-Shaw, Dose translation from animal to human studies revisited, The FASEB Journal, vol. 22, Mar. 2007, 659-661.*
International Preliminary Report on Patentability, dated Apr. 4, 2019.
Letter in Response to the Written Opinion, dated Aug. 7, 2018.
Written Opinion Of The International Searching Authority, dated Mar. 1, 2018.
Ki et al. "Senicapooc (ICA-17043): a potential therapy for theprevntion and treatment of hemolysis-associated complications in sickle cell anemia" Expert Opin Investing Drugs. Feb. 2009: 18(2):231-9. abstract.
Doupnik, "Venom-derived peptides inhibiting Kir channels: Past, present, and future", Neuropharmacology, 127 (2017), pp. 161-172.
Inoue et al. "The prevalence and impact of chronic neuropathic pain on daily and social life: A nationwide study in a Japanese population", Eur J Pain, 21 (2017), pp. 727-737.
M. P. Jensen et al., "The impact of neuropathic pain on health-related quality of life Review and implications", Neurology, Apr. 10, 2007; 68 (15), pp. 1178-1182.
R. Lu et al. "$K_{ca}$ channels modulate the processing of noxious chemical stimuli in mice", Neuropharmacology, 125 (2017), pp. 386-395.
Malliga E. Ganapathy et al., Molecular and Ligand-Binding Characterization of the ζ-Receptor in the Jurkat Human T Lymphocyte Cell Line, J Pharmacol Exper Ther, 1999, 289 (1) 251-260; https://jpet.aspetjournals.org/content/289/1/251.
Hanns Ulrich Zeilhofer, and Kay Brune, A Role for Cyclooxygenase-1 in Neuropathic Pain?, Anesthesiology 2003; 99:1043-4, https://doi.org/10.1097/00000542-200311000-00005.
Barbara J Pleuvry, Receptors, agonists and antagonists, Anaesthesia & Intensive Care Medicine 2004, 5(10), p. 350-352, https://doi.org/10.1383/anes.5.10.350.52312.
Binder A, Baron R: The pharmacological therapy of chronic neuropathic pain. Dtsch Arztebl Int 2016; 113: 616-26. DOI: 10.3238/arztebl.2016.0616.
C.J. Woolf, What is this thing called pain?, J Clin Invest. 2010;120(11):3742-3744. doi:10.1172/JCI45178.
Ryskamp et al. "Neuronal Sigma-1 Receptors: Signaling Functions and Protective Roles in Neurodegenerative Diseases" Aug. 3, 2019, vol. 13, Article 862, pp. 1-20.
Leonard BE. Sigma receptors and sigma ligands: background to a pharmacological enigma. Pharmacopsychiatry. Nov. 2004;37 Suppl 3:S166-70. doi: 10.1055/S-2004-832674. PMID: 15547782.

* cited by examiner

*Primary Examiner* — Svetlana M Ivanova
(74) *Attorney, Agent, or Firm* — Andrew Berks; Gallet Dreyer & Berkey, LLP

(57) ABSTRACT

A method is disclosed of treating pain with senicapoc, a potent $Ca^{2+}$-activated $K^+$ channel, $K_{Ca}3.1$ antagonist in CNS-resident microglia. Senicapoc is shown to cause in a decrease of IL-1β and NO release from microglia cells vivo and in vitro. Because of contribution of $K_{Ca}3.1$ to neuropathological processes, senicapoc is useful in the treatment of chronic, neuropathic, visceral, and inflammatory pain and the reversal of tactile allodynia.

2 Claims, 4 Drawing Sheets

USE OF SENICAPOC FOR TREATMENT OF NEUROPATHIC PAIN

CROSS-REFERENCE TO RELATED APPLICATIONS

This application is the U.S. National Stage of PCT International Patent Application No. PCT/US17/57930 filed Oct. 23, 2017, which claims benefit of U.S. Provisional Patent Application No. 62/412,580 filed Oct. 25, 2016 the disclosures of each of which are incorporated herein by reference in their entireties.

FIELD OF INVENTION

This invention pertains to treatment of pain with senicapoc.

BACKGROUND

Existing treatments for neuropathic pain provide effective relief to only 1 in 4 patients (Attal et al., 2010; Finnerup et al., 2015). The majority of these treatments are aimed at targets expressed by neurons of the somatosensory system (e.g. opioid receptors and the α2δ subunit 1 and 2 of voltage gated calcium channels). Expression of these targets in other areas of the CNS are believed to underlie their propensity to cause side effects such as sedation, euphoria and addiction (Finnerup et al., 2015). Recent studies have shown that non-neuronal targets expressed by activated immune cells also contribute to the establishment and maintenance of tactile allodynia in rodent models of neuropathic pain (Ren and Dubner, 2010; Scholz and Woolf, 2007; Zhuo et al., 2011). The clinical relevance of these findings was demonstrated by a recent PET study that showed an increase in PBR28 binding in the thalamus of patients with chronic low back pain (Loggia et al., 2015). PBR28 is a ligand for the translocator protein (TSPO) that increased expression in activated microglia, the CNS resident immune cells (Rupprecht et al., 2010). Collectively, the studies suggest that microglial activation may be a mechanism common to neuropathic pain models as well as patients with chronic or neuropathic pain. Targeting microglia might provide novel therapeutic options for patients with these debilitating diseases.

Mechanistically, immune cell receptor activation results in elevations of intracellular $Ca^{2+}$ concentrations which can subsequently stimulate diverse physiological responses including migration, proliferation, phagocytosis as well as production and release of cytokines, chemokines, prostanoids and reactive oxygen and nitrogen species such as nitric oxide (NO) (Hanisch, 2013). Many studies in models of neuropathic pain have demonstrated that inhibition of these immune cell receptors in the CNS (presumably on microglia) blocks the physiological sequelae of immune cell activation and ultimately pain associated behaviors (Abbadie et al.; Grace et al., 2014; Marchand et al., 2005). In microglia, one important regulator of intracellular $Ca^{2+}$ concentration is the intermediate conductance calcium-activated potassium channel $K_{Ca}3.1$ (Dale et al., 2016). The $K^+$ efflux resulting from the opening of this channel leads to the hyperpolarization of microglia which in turn facilitates $Ca^{2+}$ influx resulting in the increased and sustained stimulation of various physiological responses in vitro (Kaushal et al., 2007; Khanna et al., 2001; Schilling et al., 2004).

The contribution of $K_{Ca}3.1$ to neuropathological processes in vivo has been investigated in models of multiple sclerosis and spinal cord injury using $K_{Ca}3.1$ knock out animals as well as the $K_{Ca}3.1$ inhibitor, TRAM-34. The studies demonstrated that inhibition or loss of $K_{Ca}3.1$ function led to a reduction in lesion size as well as a reduction in cytokine levels in the CNS (Bouhy et al., 2011; Reich et al., 2005). Earlier studies in mouse models of traumatic brain injury also demonstrated that $K_{Ca}3.1$ inhibitors were neuroprotective although cytokines and other markers were not measured (Mauler et al., 2004; Urbahns et al., 2005; Urbahns et al., 2003).

Accordingly, we evaluated whether inhibition of $K_{Ca}3.1$ alleviates pain behaviors of rats with peripheral nerve injury using senicapoc, a potent, CNS penetrant inhibitor with improved stability and selectivity vs TRAM-34 (Dale et al., 2016; Schilling and Eder, 2004, 2007). Senicapoc is an experimental drug described in U.S. Pat. No. 6,288,122. Senicapoc has previously been investigated for the treatment of sickle cell anemia and malaria (Ataga et al. 2008; Tubman et al. 2016).

SUMMARY OF THE INVENTION

Senicapoc reduces $K_{Ca}3.1$ mediated $K^+$ currents and reduced the release of nitric oxide (NO) and interleukin-1β (IL-1β) from cultured rat primary microglia, and reduces pain behaviors of rats across multiple models. Moreover, senicapoc has been shown to penetrate the blood-brain barrier.

Thus, in an embodiment, a method is provided of treating chronic, neuropathic, visceral as well as inflammatory pain in patients with these conditions by the administration of an effective amount of senicapoc.

In an embodiment, a pharmaceutical composition is provided containing senicapoc for use in the treatment of chronic, neuropathic, visceral or inflammatory pain in a mammal. The mammal may be a human, or other mammal, such as a pet or livestock.

In an embodiment, the use of senicapoc is disclosed in the manufacture of a medicament for the treatment of chronic, neuropathic, visceral as well as inflammatory pain. In an embodiment, senicapoc is provided for use in reducing chronic, neuropathic, visceral as well as inflammatory pain in patients.

DETAILED DESCRIPTION

Figure 1A:
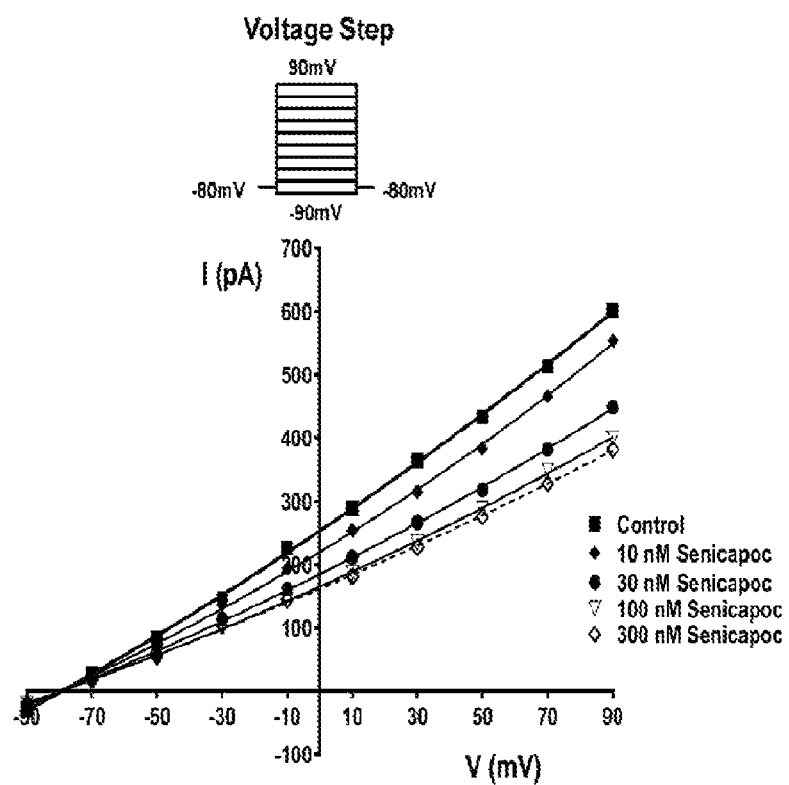
FIG. 1. $K_{Ca}3.1$ electrophysiology. $K^+$ currents were recorded from primary microglia by using either (A) depolarizing steps or (B) a voltage ramp protocol. In both paradigms, the currents reversed at 0 mV which was the equilibrium potential for $K^+$. Senicapoc dose dependently inhibited a significant part of the $K^+$ current.

The data in this study demonstrates that senicapoc is a potent blocker of the potassium channel $K_{Ca}3.1$ in rat microglia. Moreover, we found that IL-1β and NO release from cultured microglia can be regulated by senicapoc. These findings confirm that these cells express $K_{Ca}3.1$ and that inhibition of the channel regulates the release of these effector molecules. Senicapoc had an $IC_{50}$ of 10 nM in electrophysiological experiments and an $IC_{50}$ of 15 nM and 39 nM in experiments inhibiting the release of IL-1β and NO. Previous studies have demonstrated that the $K_{Ca}3.1$ inhibitor TRAM-34 can block the release of IL-1β and reactive oxygen species by microglia (Kaushal et al., 2007; Khanna et al., 2001). TRAM-34 however, is not stable and inhibits other non-selective cation channels (Dale et al., 2016; Schilling and Eder, 2004; Wulff and Castle, 2010). Another pharmacological agent, charybdotoxin, was used to assess the role of calcium activated potassium channels, however, this toxin is not selective for $K_{Ca}3.1$ as it also inhibits $K_v1.3$, $K_v1.2$ and $K_{Ca}1.1$ (de Novellis et al., 2012).

In view of the finding that senicapoc is a selective, potent antagonist of the potassium channel $K_{Ca}3.1$ in rat microglia, a method is provided of treating chronic, neuropathic, visceral as well as inflammatory pain in humans by the administration of senicapoc to a patient having chronic, neuropathic, visceral as well as inflammatory pain. In an embodiment, the use of senicapoc is provided in the manufacture of a medicament for the treatment of chronic, neuropathic, visceral as well as inflammatory pain. In an embodiment, an oral dosage form of senicapoc is provided for use in reducing chronic, neuropathic, visceral as well as inflammatory pain in patients with chronic, neuropathic, visceral as well as inflammatory pain. In an embodiment, the oral dosage form may be a tablet, capsule, or powder for dissolution or suspension in a drinkable liquid. In an embodiment, an injectable dosage form of senicapoc is provided for use in reducing chronic, neuropathic, visceral as well as inflammatory pain in patients with chronic, neuropathic, visceral as well as inflammatory pain.

Notably, when senicapoc was screened in a commercially available profiling panel at a concentration approximately 1000-fold higher than the measured $IC_{50}$ at $K_{Ca}3.1$, appreciable binding was only observed for melatonin 1A, μ- and κ-opioid receptors. Subsequent functional testing in vitro confirmed that the $IC_{50}$'s obtained for senicapoc at each receptor subtype were in the low micromolar range. Accordingly, at the doses tested here in vivo senicapoc does not achieve sufficiently high free concentrations in plasma, spinal cord or brain to engage these receptors (Table 1).

Moreover, given that senicapoc had no significant impact on rat locomotor activity when tested up to 100 mg/kg, it is likely that the reversal of injury-induced nociceptive behaviors in CCI rats (see below) did not occur merely via indiscriminate actions on motor circuits. This is important as therapeutically-relevant doses of opioids and gabapentinoids are known to impair locomotor activity in rats and to cause sedation in patients, albeit a head to head comparison of the effects of senicapoc with gabapentin on locomotor activity was not tested in the current study. The lack of significant effect at the low doses may indicate that complete inhibition of $K_{Ca}3.1$ may be required for efficacy.

Cultured microglia have been demonstrated to highly express $K_{Ca}3.1$ but these findings have not been extended to tissue given the specificity issues with available antibodies (Dale et al., 2016; Lambertsen et al., 2012). Indeed, despite testing of several anti-$K_{Ca}3.1$ antibodies, microglial specific staining in unperturbed CNS tissue has not been shown (Lambertsen et al., 2012). Some reports have suggested that $K_{Ca}3.1$ is expressed on neurons (Bouhy et al., 2011; Engbers et al., 2012; Grundemann and Clark, 2015) but these findings remain controversial (Chen et al., 2011; D'Alessandro et al., 2013; Lambertsen et al., 2012). In injured tissues however, Chen et al did demonstrate KCa3.1 staining, suggesting that expression of the channel on microglia is increased to detectable levels only upon CNS injury. As microglial activation has been well documented in models of stroke and neuropathic pain, it can be inferred that $K_{Ca}3.1$ expression may be increased in the spinal cord of rats with peripheral nerve injury. Furthermore, they are also well known to participate in inflammatory responses that lead to inflammatory pain. While inflammatory pain can often be treated with generic drugs such as the nonsteroidal anti-inflammatory drugs (NSAIDS) many of these drugs can have significant side effects including gastrointestinal bleeding. Furthermore, inflammation often accompanies many chronic and neuropathic pain conditions and contribute to the overall pain.

In addition to microglia (in vitro), $K_{Ca}3.1$ is also highly expressed in peripheral immune cells. Many studies have demonstrated the presence of peripheral immune cells such as macrophages and T cells in somatosensory nerves, dorsal root ganglia as well as the CNS following peripheral nerve injury in rodents (Marchand et al., 2005). While these immune cells are well known to express $K_{Ca}3.1$ their role in nociceptive pain processing is not as well established as for neurons or microglia.

Compounds and Formulations

Senicapoc (ICA-17043, MedChem Express, Monmouth Junction, N.J.) was dissolved at 100 mM in DMSO and diluted in media for in vitro studies. For in vivo studies, senicapoc was formulated with 20% 2-Hydroxypropyl-β-cyclodextrin (Kleptose®, Roquette, Lestrem, France) as a suspension at 10, 30 and 100 mg/kg. Gabapentin (Toronto Research Chemicals, Toronto, ON, Canada) was dissolved in saline at 100 mg/mg. All drug solutions were prepared the day of experiments. Acetonitrile (ACN), dimethyl sulfoxide (DMSO), isopropyl alcohol (IPA) and formic acid were purchased from Sigma-Aldrich (St. Louis, Mo.).

CHO-K1 Cells Expressing Recombinant Human $K_{Ca}3.1$

CHO-K1 cells stably expressing human $K_{Ca}3.1$ (Chantest, Cleveland, Ohio) were grown in T75 tissue culture flasks to 70-80% confluence (Ham's F12K and 10% Fetal Bovine Serum, Thermo Fisher). On the day of the experiment, the cells were washed with Dulbeco's Phosphate buffered saline, lifted with 2 ml of Detachin™ (Genlantis, San Diego, Calif.) and centrifuged at 250×g for 2 minutes. The supernatant was removed and the cells were washed and re-suspended in Qpatch extracellular solution to achieve a final cell density of ~3×10$^6$ cells/ml.

QPatch Electrophysiology

Whole-cell patch-clamp experiments were carried out on a QPatch-16 automated electrophysiology platform (Sophion Biosciences, Paramus, N.J.). (Jenkins et al., 2013). $K_{Ca}3.1$ channels were activated by including 10 μM free $Ca^{2+}$ in the internal patch pipette solution. Following establishment of the whole-cell configuration, cells were held at −80 mV. $K_{Ca}3.1$ current was elicited by a voltage protocol that held at −80 mV for 100 ms then stepped from −90 mV to +90 mV for 600 ms in 20 mV increments. For dose response experiments, $K_{Ca}3.1$ current was measured at 0 mV. The external solution contained (in mM): 140 NaCl, 10 HEPES, 4 KCl, $MgCl_2$, 2 $CaCl_2$ 10 Glucose (pH 7.4). The internal patch pipette solution contained (in mM): 110 K-gluconate, 34 KCl, $MgCl_2$, 5 EGTA, 10 HEPES, 4.86 $CaCl_2$ to achieve free $Ca^{2+}$ concentration of 10 μM (pH 7.2). $[Ca^{2+}]_i$ was calculated according to WEBMAX STANDARD software, http://www.stanford.edu/~cpatton/webmaxc/webmaxcS.htm. Currents were measured using the Sophion QPatch software and exported to Microsoft Excel and Prism (GraphPad, San Diego, Calif.) for further analysis.

Animals

All animal studies were conducted in accordance with the recommendations set forth in the Guide for the Care and Use of Laboratory Animals (2011) and with approval of the facility Institutional Animal Care and Use Committee. All rats received food and water ad libitum and were maintained on a 12 h light/dark cycle. For microglial cultures, E14 timed-pregnant Sprague Dawley rats were ordered (Crl:SD, Charles River, Kingston, N.Y.). For pharmacokinetic and locomotor studies, 150-175 g male Sprague Dawley rats (Crl:SD, Charles River) were purchased. For the chronic constriction injury model (CCI), twenty-five ~150 g male Sprague Dawley rats were used (Envigo, Indianapolis, Ind.). Rats were allowed to acclimate for 6-7 days prior to any in vivo procedure.

Primary Microglial Cultures

Rat primary microglia were prepared and cultured as described by Möller et al (Möller et al., 2000). Mixed glial cultures were maintained in T150 flask (Falcon—Corning, Glendale, Ariz.) in Dulbecco's modified Eagle medium (DMEM)-GlutaMax (Gibco—Thermo Fischer Scientific, Waltham, Mass.) containing 4.5 g/l of D-glucose and supplemented with 10% low endotoxin (0.06 EU/ml) heat inactivated fetal bovine serum (FBS) (Atlanta Biologicals, Lawrenceville, Ga.) and 1% penicillin/streptomycin (P/S) (Gibco). Cultures were grown in a humidified incubator at 37° C. under 5% $CO_2$ for 10-14 days at which time they were harvested by tapping the flasks and collecting the microglia-containing medium. Microglia were pelleted by centrifugation at 276×g for 5 min, re-suspended in DMEM/10% FBS/PS medium and plated at desired density in poly-d-lysine (PDL)-coated plates (BioCoat—Corning). Purity was assessed by labeling with the microglial maker CD11b, which identified >95% of cells as microglia.

Microglial IL-1β Release

Rat primary microglia were primed with 3 EU/mL of ultra-pure Lipopolysaccharide (control standard endotoxin (CSE) Associates of Cape Cod, Falmouth, Mass.). After 3.5 hours, vehicle or senicapoc were added and allowed to incubate for 30 minutes. Finally, BzATP (1 mM; Sigma-Aldrich, St. Louis, Mo.) was added to activate P2X7 receptors and trigger release of IL-1β (BzATP also inhibits other receptors such as P2X4 receptors). Cell free supernatants were assayed for IL-1β using a custom rat cytokine assay (N451A-1; MesoScale Discovery, Rockville, Md.). $IC_{50}S$ were determined using Prism (Graphpad, San Diego, Calif.)

Microglial NO Release (Measurement of Nitrite)

Rat primary microglia were pre-incubated with vehicle or senicapoc for 30 minutes. Next, 3 EU/ml of ultra-pure Lipopolysaccharide (CSE, Associates of Cape Cod) was added to induce iNOS expression and NO synthesis. After a total incubation time of 24 hours, media was collected, spun down to remove cells and assayed for nitrite (the stable breakdown product of NO) using Griess Reagent (Promega, Madison Wis.).

Electrophysiology Recordings in Primary Microglia

Primary rat microglia were plated at a density of 300,000/35 mm dish for 24 hours. Whole cell patch clamp recordings were performed using an EPC9 patch-clamp amplifier and PatchMaster software (HEKA Instruments Inc.). The cell's membrane potential was held at −60 mV. External solution contained (in mM): 140 NaCl, 4 KCl, $MgCl_2$, 1.8 $CaCl_2$, 10 HEPES, 10 Glucose, pH 7.4. Patch solution contained (in mM): 140 $CsCl_2$, 11 EGTA, 2 $MgCl_2$, 10 HEPES, pH 7.2. Drugs were applied by gravity and selected with a capillary tube placed in close proximity to the recording dish. BzATP (Sigma-Aldrich, St. Louis, Mo.) was applied for 10 seconds.

Determination of Rat Plasma, Brain and Spinal Cord Exposure and Free Concentration Determination Male Sprague-Dawley rats (Crl:SD, Charles River) weighing 200-350 g were dosed to determine tissue exposure at 10 mg/kg p.o. (n=3) for screening pharmacokinetics (PK), and at 10, 30 and 100 mg/kg p.o. for the CCI studies (n=3 from each treatment group taken from the last arm of study). In order to confirm the pharmacokinetics of senicapoc, animals were subjected to deep anesthesia with ketamine to obtain CSF via cisternal puncture at 1 h and 4 h post dosing with senicapoc. The rats were then decapitated and trunk blood was collected to in $K_3EDTA$ containing tubes. Plasma samples were generated by centrifugation (3500×g), and stored frozen at −20° C. until bioanalysis. The brains were harvested immediately following blood collection and stored frozen until bioanalysis at −20° C. For CCI animals, the plasma and brain harvests as described for the screening PK, although the tissue collection was initiated after the behavioral assessment was completed, approximately 4 hours 15 minutes after dosing. For spinal column harvest, a 20-gauge needle on a 10 ml syringe filled with cold saline was inserted into the spinal cord. The saline was used to flush the spinal column out. The spinal column tissues were then stored frozen at −20° C. prior to exposure measurements. Total senicapoc tissue concentrations were determined at Primera Analytical Solutions Corporation (Princeton, N.J.) as described in next section.

Bioanalysis of Plasma, Brain and Spinal Cord Tissues

Senicapoc concentrations in plasma, brain and spinal cord samples were determined using an LC-10ADVP (Schimadzu) coupled with mass spectrometry (AB Sciex 4000). Prior to analysis, the brain and spinal cord samples were thawed at room temperature, weighed and homogenized using a homogenizing solution ($IPA/H_2O/DMSO$; 30:50:20) at a ratio of 3/1 (ml/g) to generate tissue homogenates. An aliquot of 50 µl plasma, or 50 µl brain and spinal cord homogenates is mixed with 150 µl of a DMSO/ACN (20:80) solution that contains an internal standard (50 ng/ml). The diluted plasma, brain and spinal cord sample is then centrifuged (~500 g for 15 min at 10° C.), supernatant is removed and then injected (10 µl) onto LC/MS/MS system for analysis. An Atlantis T3 column 2.6µ C18, 50×2.1 mm (Waters, Mass.) was used for analytical separation of the acid. A 6-minute mobile phase gradient was employed with mobile phase A (0.1% formic acid in water) ramping down from 99% to 1% (0-4 minutes), and then ramping back up to 99% (4-6 minutes), while ramping up solvent B (1% formic acid in ACN), from 1% to 99% (0-4 minutes), and then ramping down to 1% (4-6 minutes). Spectra was acquired in positive SRM mode with the parent mass of 324 and a daughter ion of 228.

Determination of Plasma and Brain Free Fraction

The unbound plasma fraction (UBP) or unbound brain fraction (UBBr) of senicapoc were determined in vitro utilizing an equilibrium dialysis method modified slightly from a previously described method (Kalvass and Maurer, 2002). Briefly, naive plasma and brain tissues were homogenized in 3× and 4× w/v in homogenization buffer (50:30:20 $H_2O:IPA:DMS0$), respectively. Senicapoc (10 µM) stock solution in DMSO was added to the naive plasma or brain homogenates and subsequently dialyzed against 0.01 M phosphate buffer for 2.5 h with a semipermeable membrane (MW cutoff 2000 Da) using a 96-well HTDialysis Teflon block apparatus (Gales Ferry, Conn.) incubated at 37° C. in 5% $CO_2$. Following equilibration, the buffer sample was fortified with a fixed volume of blank tissue homogenate and the tissue sample was fortified with a fixed volume of buffer. Protein precipitation was performed with ice cold acetonitrile in the presence of an analytical internal standard. The supernatants were quantified for senicapoc using LC-MS/MS as described earlier. The senicapoc "Fraction unbound" was calculated by dividing the peak area response (peak area of analyte/peak area of internal standard) in the buffer compartment by the peak area response in the tissue compartment followed by correcting the dilution factor using the equation suggested by Watson et al. (Watson et al., 2009).

Chronic Constriction Injury (CCI) Surgery and Behavioral Testing

Peripheral nerve injury was performed according to the method of Bennett and Xie (Bennett and Xie, 1988), with paw withdrawal thresholds to Von Frey filament stimulation measured as described previously (Chaplan et al., 1994; Tal and Bennett, 1994).

Figure 4:
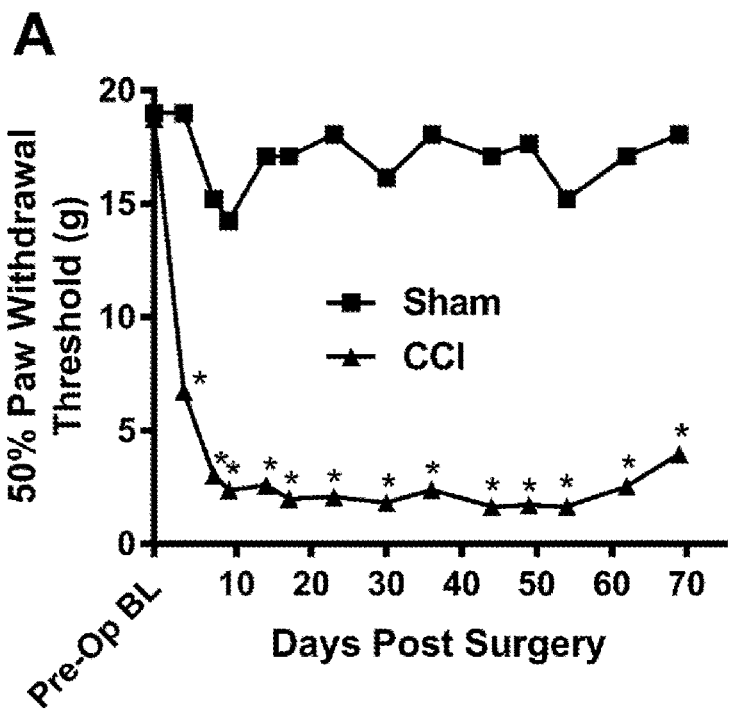
FIG. 4. Time course and efficacy of senicapoc in the CCI model. Following nerve injury, CCI rats displayed a marked reduction in the 50% paw withdrawal threshold (g) in response to von Frey stimulation of the injured hind paw compared with their Pre-Op baseline and sham rats. (A) This mechanical allodynia was evident from as early as Day 3 post surgery and was maintained throughout the duration of the experiment. Data are mean+/−S.E.M. n=8 in sham group and n=11 in the CCI cohort. *P<0.05 vs sham (two-way repeated measure ANOVA followed by Bonferroni's post test). (B) In a second cohort of rats, the 50% paw withdrawal threshold (g) in response to von Frey stimulation of the injured hind paw was determined in CCI rats (n=12/group) dosed with either vehicle, senicapoc (SEN) or gabapentin (GBP). The efficacy of senicapoc (10, 30 and 100 mg/kg, p.o.) was evaluated at its $T_{max}$, 4 hours after dosing. For vehicle and gabapentin (100 mg/kg), thresholds were determined at 2 hours after administration of 100 mg/kg. Gabapentin significantly reversed the mechanical hypersensitivity of nerve injured rats (66% reversal). The $K_{Ca}3.1$ inhibitor (senicapoc) also reversed the tactile allodynia at 100 mg/kg (48% reversal). Data were analyzed by one-way ANOVA followed by Fisher's post-hoc comparison. *p<0.0001 vs vehicle.
Figure 4:
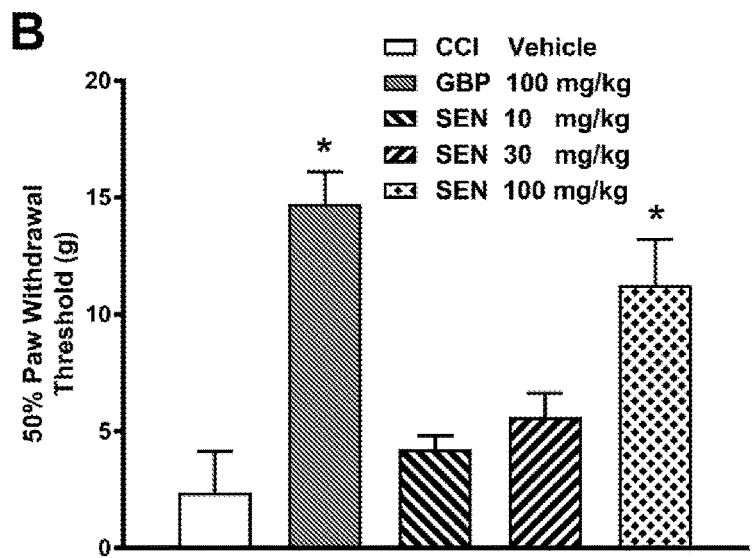

In the first cohort of nerve injured rats, hindpaw mechanical hypersensitivity was evident by day 7 and maintained for the duration of the experiment (see FIG. 4A). Pharmacological studies with gabapentin and senicapoc were performed on a second cohort of CCI rats with established hind paw mechanical hypersensitivity between days 14-63 post injury. Experiments were run using a simple cross-over design. Tactile hypersensitivity of rats was evaluated one day prior to drug testing. Drugs were allowed to wash out for one week at which time the mechanical hypersensitivity was reassessed. Rats were then randomly re-assigned to groups prior to the next arm of the study being run. In the final arm, tissue was collected from 3 animals from each group immediately after behavioral assessment of allodynia. Dosing of drugs, assessment of mechanical thresholds and collection of tissues were performed by individual experimenters all blinded to treatments.

All CCI data are presented as mean+/−S.E.M. and were analyzed using ANOVA followed by Fisher's PLSD post-hoc analysis (StatView, Cary, N.C.) when appropriate.

Rat Locomotor Activity

Male Sprague-Dawley rats (Charles River) weighing 225-275 g on the test day were divided into groups of 8 animals per treatment. Senicapoc was administered p.o. at doses indicated 4 hours prior to the start of locomotor activity testing. Following the pre-treatment time, rats were placed into 50×25×20 cm cages lined with crushed corn cob bedding (Bed-o'Cobs ¼ inch, Andersons Lab Bedding, Maumee, Ohio, USA). The cages were positioned in a Smart Frame Cage Rack (Kinder Scientific, Poway, Calif., USA) outfitted with an infrared beam array (7 X×15 Y). Rats were allowed to move freely within the cage for 1 hour with beam breaks continuously recorded using MotorMonitor™ (Kinder Scientific,). Time course and cumulative data were analyzed with Prism 4 (GraphPad, La Jolla, Calif.). One-way ANOVA with Tukey's Multiple Comparison Post-Hoc Test was used for statistical analysis.

Off Target Screen of Senicapoc

Screening of senicapoc in vitro against a commercial panel of 50 neuronal receptors, 8 enzymes, 5 transporters was contracted out to CEREP (Celle-Lévescault, France http://www.cerep.fecerep/users/pages/ProductsServices/pharmacoetADME.asp) and 7 $K_{Ca}3.1$-relevant ion channels was contracted out to Chantest (Cleveland, Ohio) respectively.

Figure 1B:
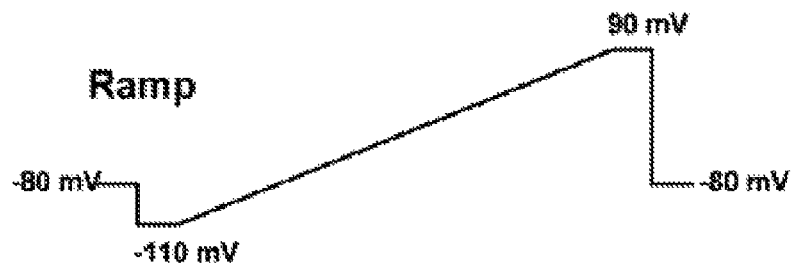
Figure 1B:
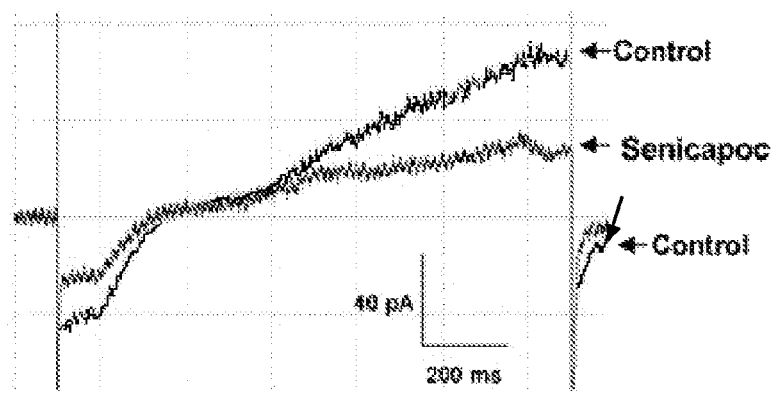

Senicapoc Inhibits $K^+$ Currents in Rat Primary Microglia $K_{Ca}3.1$ is highly expressed on microglia in vitro (Kaushal et al., 2007). The effect of senicapoc was evaluated on microglial K$^+$ currents elicited by either depolarizing steps (FIG. 1A) or a voltage ramp protocol (FIG. 1B) using automated patch clamp analysis. Senicapoc dose dependently (10, 100, 300 and 1000 nM) inhibited the microglial K$^+$ current although not completely (FIG. 1A) with an IC$_{50}$ of 10 nM. This value is in close agreement with the IC$_{50}$ value (10 nM) generated by patch-clamp studies on CHO-K$_{Ca}$3.1 cells. Some residual K$^+$ current still remained which was most likely not K$_{Ca}$3.1-sensitive (Kettenmann et al., 2011)

Figure 2:
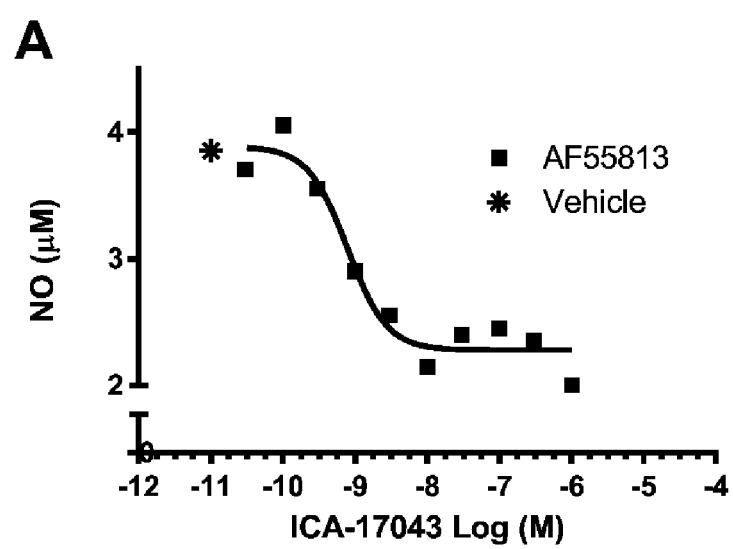
FIG. 2. Effect of $K_{Ca}3.1$ inhibition on NO and IL-1β release from primary microglia. (A) Primary rat cortical microglia were pre-treated with vehicle or senicapoc at concentrations indicated for 30 minutes followed by addition of LPS (3EU/ml) and incubated for a total of 24 hours. Senicapoc inhibited the production of NO (as measured by its metabolite, nitrite) with an $EC_{50}$ of 0.9 nM as shown in a representative experiment (n=3). (B) Primary rat cortical microglia were incubated with LPS (3EU/ml) for 24 hours to induce expression of IL-1β. Senicapoc dose dependently inhibited IL-1β release from primary microglia with an $IC_{50}$ of 1.3 nM (n=3).
Figure 2:
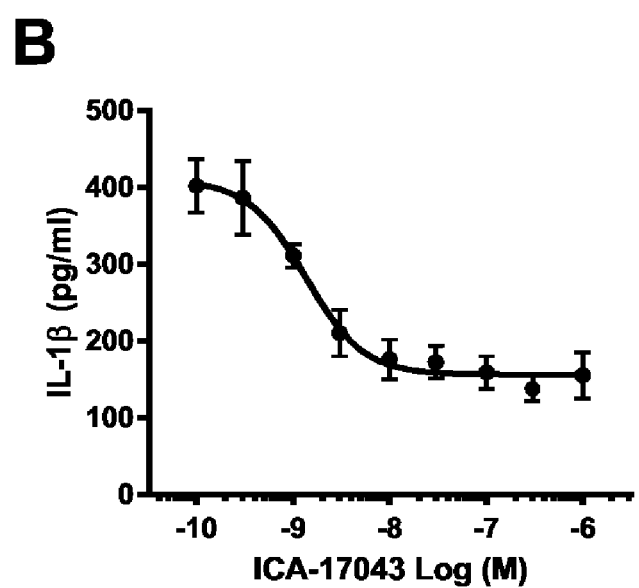

Inhibition of K$_{Ca}$3.1 by Senicapoc Blocks the Release of NO and IL-1β From Primary Rat Microglia Primary rat cortical microglia were incubated with either vehicle or senicapoc for 30 minutes prior to the addition of vehicle or ultrapure LPS (3 EU/ml) to stimulate iNOS expression and NO release. After 24 hours, media was assayed for nitrite (stable metabolite of NO). Senicapoc dose dependently inhibited the release of NO from LPS-treated microglia with an average IC$_{50}$ of 39 nM (FIG. 2A), in agreement with previous studies (Kaushal et al., 2007; Khanna et al., 2001). Primary rat cortical microglia were also treated with LPS (3 EU/ml, 3 hours) to stimulate the production of pro-IL-1β. Next, vehicle or senicapoc were added and incubated for an additional 30 minutes followed by the addition of BzATP (1 mM) to activate P2X7 receptors and trigger the activation of caspase 1, its cleavage pro-IL-1β and the release of the liberated IL-1β (another 30 minutes). Senicapoc dose dependently inhibited IL-1β release from primary microglia with an IC$_{50}$ of 15 nM (FIG. 2B).

Pharmacokinetics of Senicapoc

The peripheral pharmacokinetics of senicapoc in rats has been evaluated previously (McNaughton-Smith et al., 2008). Senicapoc had oral bioavailability of 51% with maximum plasma concentration (C$_{max}$) achieved at 4 hours (T$_{max}$) post dose; however, CNS penetrance had not been evaluated. To improve our understanding of the utility of senicapoc as a tool compound to block K$_{Ca}$3.1 on microglia in the CNS, we measured the levels of senicapoc in the brain, CSF and plasma of rats at 1 and 4 hours after administration. At 10 mg/kg oral dose, senicapoc had a good free brain to free plasma ratio of 2.2 and 2.1 at 1 and 4 h post dose, respectively. Senicapoc showed good systemic distribution with average free plasma concentrations of 17 and 65 nM at 1 and 4 hours, respectively (Table 1). The average free brain concentrations achieved were 37 nM and 136 nM at 1 and 4 hours, respectively. The average measured CSF concentrations were 25 and 121 nM at 1 and 4 hours respectively, similar to what was determined for free brain, indicating the likely establishment of CNS distribution equilibrium of senicapoc by 1-hour post dose. Free brain concentrations at 10 mg/kg were approximately 4- and 14-fold higher at 1 and 4 hours post dose than the IC$_{50}$ (10 nM) generated in by patch-clamp studies in microglia. Furthermore, at 1 and 4 hours, the free brain concentrations were 8- and 10-fold higher than the IC$_{50}$ (15 nM) of senicapoc in the primary microglial IL-1β release assay. This also demonstrates that there is sufficient K$_{Ca}$3.1 target coverage of senicapoc in the CNS.

TABLE 1

Senicapoc Plasma, Brain and Spinal Cord Exposure and Free Concentration Profile in Rat Screening Pharmacokinetics (PK) and Constriction Injury (CCI) Model

| | Screening PK (Mean ± SD) | | CCI (Mean ± SD) | | |
|---|---|---|---|---|---|
| PO Dose (mg/kg)* | 10 | 10 | 10 | 30 | 100 |
| Time (h) | 1 | 4 | 4 | 4 | 4 |
| Plasma (nM) | 637 ± 322 | 2394 ± 748 | 782$^£$ | 2055 ± 452 | 3804 ± 93 |
| Brain (nM) | 4661 ± 1986 | 16917 ± 6040 | 2774 ± 380 | 6417 ± 1958 | 13299 ± 2625 |
| CSF (nM) | 25 ± 16 | 121 ± 62 | ND | ND | ND |
| Free Plasma (nM)** | 17 ± 9 | 65 ± 22 | 21$^£$ | 56 ± 12 | 103 ± 3 |
| Free Brain (nM)*** | 37 ± 16 | 136 ± 50 | 22 ± 1 | 51 ± 16 | 106 ± 21 |
| Free Brain/Free Plasma | 2.2 ± 0.4 | 2.1 ± 0.4 | 1.1 ± 0.1 | 0.9 ± 0.1 | 1.0 ± 0.2 |
| Spinal Cord (nM) | ND | ND | <LLQ$^γ$ | 3404 ± 2743 | 11905 ± 2182 |
| Free Spinal Cord (nM)$^¶$ | ND | ND | ND | 38 ± 17 | 95 ± 17 |
| Free Spinal Cord/Free Plasma | ND | ND | ND | 0.8 ± 0.6 | 0.7 ± 0.3 |
| Free Brain/IC$_{50}$$^π$ | 3.7 | 13.6 | 1.7 | 5.1 | 10.6 |
| Free Spinal Cord/IC$_{50}$$^π$ | ND | ND | ND | 3.8 | 9.5 |

*n = 3;
**In vitro rat plasma free fraction (UBP = 0.027) used for free plasma calculation;
***In vitro rat brain free fraction (UBBr = 0.008) used for free brain calculation;
$^¶$Used brain free fraction (UBBr = 0.008) to calculate free spinal cord (UBSc), assuming similar free fraction based on data generated for other in-house compounds (data not shown);
$^π$Used 10 nM IC$_{50}$, from CHO-K$_{Ca}$3.1 patch clamp assay;
$^£$n = 1(remaining 2 samples <LLQ (773 nM);
$^γ$All <LLQ (773 nM);
ND—Not Determined Pharmacological Activity of Senicapoc in Rodents The potency of Senicapoc in reducing acute and tonic pain, neuropathic pain, inflammatory pain, post-operative pain and visceral pain was evaluated by comparing semicopac to other well known pain medications such as Morphine, Gabapentin, Indomethacin and (–)U50 488 H. Senicapoc 100 mg/kg was compared to Morphine 4 mg/kg for treatment of acute and tonic pain, neuphatic pain and post-operative pain, to Gabapentin 100 mg/kg for treatment of neurophatic pain, to Indomethacin 30 mg and 10 mg/kg for treatment of inflammatory pain and to (–)U50 488 H 3 mg/kg for treatment of visceral pain. The results show that Senicapoc treated animals have lower sensitivity to in models of chronic, neuropathic, visceral as well as inflammatory pain 240 min after treatment (Table 2). Depending on the test, the percentage of activity was calculated from the mean value of the vehicle-treated animals and compared to naïve animals, control paw or cut-off value.

Senicapoc (10, 30 and 100 mg/kg, p.o.) was tested in the same cohort of CCI rats with the positive control gabapentin (100 mg/kg, p.o.), using a simple cross-over design. $K_{Ca}3.1$ inhibition with senicapoc at 100 mg/kg significantly reversed the mechanical hypersensitivity of nerve injured

TABLE 2

Rodent Efficiency Testing

| Pain Area | Model-Test | Senicapoc 100 mg/kg PO % of activity vs. vehicle | Internal Reference Reference drug | % of activity vs. vehicle |
|---|---|---|---|---|
| Acute & Tonic pain | Healthy rats - Paw pressure test | −12% | Morphine 4 mg/kg s.c. | 69% |
| | Healthy rats - Tail flick test | 9% | Morphine 4 mg/kg s.c. | 66% |
| | Acetic acid test - Abdominal cramps | −32% | (−) U50, 488 H 3 mg/kg s.c. | 100% |
| | Formalin test - Score (early phase) | 14% | Morphine 4 mg/kg s.c. | 57% |
| | Formalin test - Score (late phase) | 8% | Morphine 4 mg/kg s.c. | 38% |
| Neuropathic Pain | Bennett model - Paw pressure test | 69% | Morphine 4 mg/kg s.c. | 191% |
| | Oxaliplatin - Acetone test (reaction time) | 68% | Gabapentin 100 mg/kg p.o. | 82% |
| Inflammatory pain | Carrageenan - Paw pressure test | 116% | Indomethacin 30 mg/kg p.o. | 100% |
| | Kaolin - Gait score | 29% | Indomethacin 10 mg/kg p.o. | 58% |
| Post-operative pain | Brennan model - Electronic Von Frey test | −7% | Morphine 4 mg/kg s.c. | 88% |
| Visceral pain | TNBS - Colorectal distension | 50% | (−) U50, 488 H 3 mg/kg s.c. | 103% |
| Behaviour & Acute toxicity | Irwin grid | No effect | | |

Testing: 240 min after treatment.
n = 4/model/test
Results are expressed for each group as a percentage of activity calculated from the mean value of the vehicle-treated animals and compared to naïve animals, control paw or cut-off value, depending on the test (from the ANS Biotech historical database).

Off Target and Side Effect Profile of Senicapoc

Figure 3:
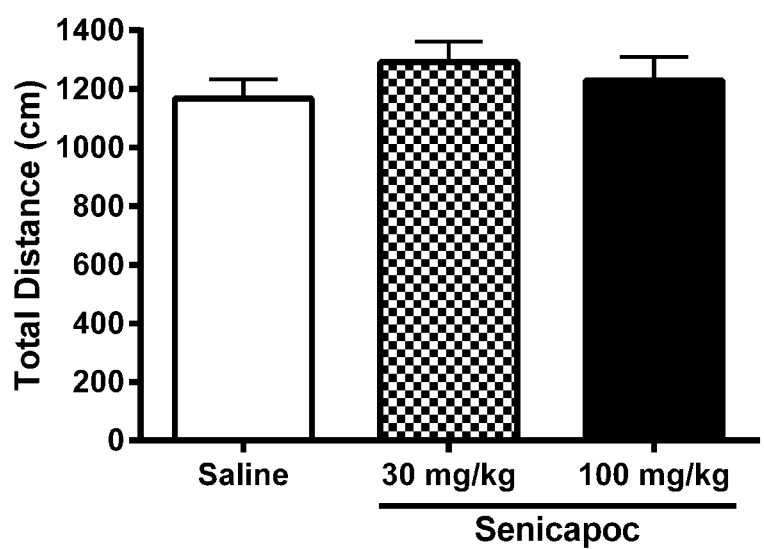
FIG. 3. Effect of senicapoc on locomotor activity. In order to evaluate the potential CNS side effects of senicapoc, rats were dosed at 30 and 100 mg/kg and assessed in the locomotor activity assay 4 hours later. Senicapoc had no effect on the total distance the rats traveled at either 30 or 100 mg/kg, p.o. (n=3). Data were analyzed by one-way ANOVA. None of the differences were significant.

Senicapoc was screened in vitro at 10 μM against a commercially available panel of 50 neuronal receptors, 8 enzymes, 5 transporters by CEREP and 7 ion channels by Chantest. Of these drug discovery relevant targets senicapoc inhibited only melatonin 1A receptors and μ- and κ-opioid receptors more than 50%. The $IC_{50}S$ for these targets were confirmed in a full dose response curve and determined to be 1.7, 12 and 19 μM respectively, well above the $IC_{50}$ values of senicapoc on $K_{Ca}3.1$ channels, i.e. 10 nM. To assess any overt sedating effects, a frequent side effect of current pain medications, senicapoc was evaluated in the locomotor activity assay at 30 and 100 mg/kg p.o. Senicapoc did not significantly affect the locomotor activity of rats at either dose tested (FIG. 3).

Time Course of CCI Model of Peripheral Nerve Injury and Dose Dependent Efficacy of Senicapoc To test whether $K_{Ca}3.1$ plays a role in the maintenance of mechanical hypersensitivity following peripheral nerve injury we first determined the onset as well as the duration of hind paw mechanical hypersensitivity in rats with chronic constriction injury (CCI) of the sciatic nerve (CCI). Mechanical hypersensitivity was evident by day 7 and maintained for the duration of the experiment (see FIG. 4A).

rats by 48%. The positive control, gabapentin, also significantly reduced the tactile allodynia by 66% (FIG. 4B).

Interestingly, a significantly lower tissue exposure profile of senicapoc was observed in CCI animals in comparison to naïve rats (Table 1). The difference may be attributed to changes in pharmacokinetics of senicapoc in animals with CCI. However, there was sufficient free drug in CNS tissues (brain and spinal cord) with tissue to plasma disposition ratios similar to naïve animals providing free drug concentrations ~11-fold higher than the in vitro $IC_{50}$ (10 nM) from patch clamp studies in agreement with the observed reversal of tactile allodynia at 100 mg/kg (Table 1).

CONCLUSIONS

Senicapoc reduced $K_{Ca}3.1$ mediated $K^+$ currents and reduced the release of NO and IL-1β from cultured rat primary microglia. In vivo we have shown that senicapoc significantly reverses neuropathic hypersensitivity in CCI rats with efficacy comparable to gabapentin. Importantly, senicapoc did not impair locomotor function in rats. This data suggests that selective inhibition of $K_{Ca}3.1$ by senicapoc will be a novel and effective treatment for neuropathic pain.

DOSAGE FORMS

Senicapoc may be formulated as an oral or injectable pharmaceutical formulation product for use in chronic, neuropathic, visceral as well as inflammatory pain.

Oral dosage forms include tablets, capsules, and powders for dissolution or suspension in a drink. Such tablets and capsules may be formulated by any of various methods known in the art, and may include at least one excipient.

Injectable forms may be formulated for intramuscular or intravenous use. Such injectable formulations may be formulated by any of various methods known in the art, and may include at least one excipient.

REFERENCES

Guide for the Care and Use of Laboratory Animals (2011) 8th ed, Washington (DC). Abbadie, C., Bhangoo, S., De Koninck, Y., Malcangio, M., Melik-Parsadaniantz, S., White, F. A., 2009. Chemokines and pain mechanisms. Brain Res Rev 60, 125-134.

Ataga K I, Smith W R, De Castro L M, Swerdlow P, Saunthararajah Y, Castro O, Vichinsky E, Kutlar A, Orringer E P, Rigdon G C, Stocker J W, (2008) Efficacy and safety of the Gardos channel blocker, senicapoc (ICA-17043), in patients with sickle cell anemia, Blood 111:3991-3997; doi: https://doi.org/10.1182/blood-2007-08-110098

Attal, N., Cruccu, G., Baron, R., Haanpaa, M., Hansson, P., Jensen, T. S., Nurmikko, T., 2010. EFNS guidelines on the pharmacological treatment of neuropathic pain: 2010 revision. Eur J Neurol 17, 1113-e1188.

Bennett, G. J., Xie, Y. K., (1988). A peripheral mononeuropathy in rat that produces disorders of pain sensation like those seen in man. Pain 33, 87-107.

Bouhy, D., Ghasemlou, N., Lively, S., Redensek, A., Rathore, K. I., Schlichter, L. C., David, S., (2011). Inhibition of the Ca(2)(+)-dependent K(+) channel, KCNN4/$K_{Ca}3.1$, improves tissue protection and locomotor recovery after spinal cord injury. J Neurosci 31, 16298-16308.

Chaplan, S. R., Bach, F. W., Pogrel, J. W., Chung, J. M., Yaksh, T. L., (1994). Quantitative assessment of tactile allodynia in the rat paw. J Neurosci Methods 53, 55-63.

Chen, Y. J., Raman, G., Bodendiek, S., O'Donnell, M. E., Wulff, H., (2011). The $K_{Ca}3.1$ blocker TRAM-34 reduces infarction and neurological deficit in a rat model of ischemia/reperfusion stroke. J Cereb Blood Flow Metab 31, 2363-2374.

D'Alessandro, G., Catalano, M., Sciaccaluga, M., Chece, G., Cipriani, R., Rosito, M., Grimaldi, A., Lauro, C., Cantore, G., Santoro, A., Fioretti, B., Franciolini, F., Wulff, H., Limatola, C., (2013). KCa3.1 channels are involved in the infiltrative behavior of glioblastoma in vivo. Cell Death Dis 4, e773.

Dale, E., Staal, R. G., Eder, C., Moller, T., (2016). KCa3.1-a microglial target ready for drug repurposing? Glia 64, 1733-1741.

de Novellis, V., Luongo, L., Guida, F., Cristino, L., Palazzo, E., Russo, R., Marabese, I., D'Agostino, G., Calignano, A., Rossi, F., Di Marzo, V., Maione, S., (2012). Effects of intra-ventrolateral periaqueductal grey palmitoylethanolamide on thermoceptive threshold and rostral ventromedial medulla cell activity. Eur J Pharmacol 676, 41-50.

Engbers, J. D., Anderson, D., Asmara, H., Rehak, R., Mehaffey, W. H., Hameed, S., McKay, B. E., Kruskic, M., Zamponi, G. W., Turner, R. W., (2012). Intermediate conductance calcium-activated potassium channels modulate summation of parallel fiber input in cerebellar Purkinje cells. Proc Natl Acad Sci U.S.A 109, 2601-2606.

Finnerup, N. B., Attal, N., Haroutounian, S., McNicol, E., Baron, R., Dworkin, R. H., Gilron, I., Haanpaa, M., Hansson, P., Jensen, T. S., Kamerman, P. R., Lund, K., Moore, A., Raja, S. N., Rice, A. S., Rowbotham, M., Sena, E., Siddall, P., Smith, B. H., Wallace, M., (2015). Pharmacotherapy for neuropathic pain in adults: a systematic review and meta-analysis. Lancet Neurol 14, 162-173.

Grace, P. M., Hutchinson, M. R., Maier, S. F., Watkins, L. R., (2014). Pathological pain and the neuroimmune interface. Nat Rev Immunol 14, 217-231.

Grundemann, J, Clark, B. A., (2015). Calcium-Activated Potassium Channels at Nodes of Ranvier Secure Axonal Spike Propagation. Cell Rep 12, 1715-1722.

Hanisch, U. K., (2013). Functional diversity of microglia—how heterogeneous are they to begin with? Front Cell Neurosci 7, 65.

Jenkins, D. P., Yu, W., Brown, B. M., Lojkner, L. D., Wulff, H., (2013). Development of a QPatch automated electrophysiology assay for identifying KCa3.1 inhibitors and activators. Assay Drug Dev Technol 11, 551-560.

Kalvass, J. C., Maurer, T. S., (2002). Influence of nonspecific brain and plasma binding on CNS exposure: implications for rational drug discovery. Biopharmaceutics & drug disposition 23, 327-338.

Kaushal, V., Koeberle, P. D., Wang, Y., Schlichter, L. C., (2007). The Ca2+-activated K+ channel KCNN4/KCa3.1 contributes to microglia activation and nitric oxide-dependent neurodegeneration. J Neurosci 27, 234-244.

Kettenmann, H., Hanisch, U. K., Noda, M., Verkhratsky, A., (2011). Physiology of microglia. Physiol Rev 91, 461-553.

Khanna, R., Roy, L., Zhu, X., Schlichter, L.C., (2001). K+channels and the microglial respiratory burst. Am J Physiol Cell Physiol 280, C796-806.

Lambertsen, K. L., Gramsbergen, J. B., Sivasaravanaparan, M., Ditzel, N., Sevelsted-Moller, L. M., Olivan-Viguera, A., Rabjerg, M., Wulff, H., Kohler, R., (2012). Genetic KCa3.1-deficiency produces locomotor hyperactivity and alterations in cerebral monoamine levels. PLoS One 7, e47744.

Loggia, M. L., Chonde, D. B., Akeju, O., Arabasz, G., Catana, C., Edwards, R. R., Hill, E., Hsu, S., Izquierdo-Garcia, D., Ji, R. R., Riley, M., Wasan, A. D., Zurcher, N. R., Albrecht, D. S., Vangel, M. G., Rosen, B. R., Napadow, V., Hooker, J. M., (2015). Evidence for brain glial activation in chronic pain patients. Brain 138, 604-615.

Marchand, F., Perretti, M., McMahon, S. B., (2005). Role of the immune system in chronic pain. Nat Rev Neurosci 6, 521-532.

Mauler, F., Hinz, V., Horvath, E., Schuhmacher, J., Hofmann, H. A., Wirtz, S., Hahn, M. G., Urbahns, K., (2004). Selective intermediate-/small-conductance calcium-activated potassium channel (KCNN4) blockers are potent and effective therapeutics in experimental brain oedema and traumatic brain injury caused by acute subdural haematoma. Eur J Neurosci 20, 1761-1768.

McNaughton-Smith, G. A., Burns, J. F., Stocker, J. W., Rigdon, G. C., Creech, C., Arrington, S., Shelton, T., de Franceschi, L., (2008). Novel inhibitors of the Gardos channel for the treatment of sickle cell disease. J Med Chem 51, 976-982.

Moller, T., Hanisch, U.K., Ransom, B. R., (2000). Thrombin-induced activation of cultured rodent microglia. J Neurochem 75, 1539-1547.

Reich, E. P., Cui, L., Yang, L., Pugliese-Sivo, C., Golovko, A., Petro, M., Vassileva, G., Chu, I., Nomeir, A. A., Zhang, L. K., Liang, X., Kozlowski, J. A., Narula, S. K., Zavodny, P. J., Chou, C. C., (2005). Blocking ion channel KCNN4 alleviates the symptoms of experimental autoimmune encephalomyelitis in mice. Eur J Immunol 35, 1027-1036.

Ren, K., Dubner, R., (2010). Interactions between the immune and nervous systems in pain. Nat Med 16, 1267-1276.

Rupprecht, R., Papadopoulos, V., Rammes, G., Baghai, T. C., Fan, J., Akula, N., Groyer, G., Adams, D., Schumacher, M., (2010). Translocator protein (18 kDa) (TSPO) as a therapeutic target for neurological and psychiatric disorders. Nat Rev Drug Discov 9, 971-988.

Schilling, T., Eder, C., (2004). A novel physiological mechanism of glycine-induced immunomodulation: Na+-coupled amino acid transporter currents in cultured brain macrophages. J Physiol 559, 35-40.

Schilling, T., Eder, C., (2007). TRAM-34 inhibits nonselective cation channels. Pflugers Arch 454, 559-563.

Schilling, T., Stock, C., Schwab, A., Eder, C., (2004). Functional importance of Ca2+-activated K+ channels for lysophosphatidic acid-induced microglial migration. Eur J Neurosci 19, 1469-1474.

Scholz, J., Woolf, C. J., (2007). The neuropathic pain triad: neurons, immune cells and glia. Nat Neurosci 10, 1361-1368.

Tal, M., Bennett, G. J., (1994). Extra-territorial pain in rats with a peripheral mononeuropathy: mechano-hyperalgesia and mechano-allodynia in the territory of an uninjured nerve. Pain 57, 375-382.

Venée N. Tubman, Pedro Mejia, Boris E. Shmukler, Amy K. Bei, Seth L. Alper, James R. Mitchell, Carlo Brugnara, and Manoj T. Duraisingh (2016). The Clinically Tested Gardos Channel Inhibitor Senicapoc Exhibits Antimalarial Activity, Antimicrob Agents Chemother. Jan; 60(1): 613-616; Published online 2015 Dec. 31. Prepublished online 2015 Oct. 12. doi: 10.1128/AAC.01668-15

Urbahns, K., Goldmann, S., Kruger, J., Horvath, E., Schuhmacher, J., Grosser, R., Hinz, V., Mauler, F., (2005). IKCa-channel blockers. Part 2: discovery of cyclohexadienes. Bioorganic & medicinal chemistry letters 15, 401-404.

Urbahns, K., Horvath, E., Stasch, J. P., Mauler, F., (2003). 4-Phenyl-4H-pyrans as IK(Ca) channel blockers. Bioorganic & medicinal chemistry letters 13, 2637-2639.

Watson, J., Wright, S., Lucas, A., Clarke, K. L., Viggers, J., Cheetham, S., Jeffrey, P., Porter, R., Read, K. D., (2009). Receptor occupancy and brain free fraction. Drug metabolism and disposition: the biological fate of chemicals 37, 753-760.

Wulff, H., Castle, N. A., (2010). Therapeutic potential of $K_{Ca}3.1$ blockers: recent advances and promising trends. Expert Rev Clin Pharmacol 3, 385-396.

Zhuo, M., Wu, G., Wu, L. J., (2011). Neuronal and microglial mechanisms of neuropathic pain. Mol Brain 4, 31.

The invention claimed is:

1. A method of inhibiting $K_{Ca}3.1$ calcium activated potassium channels on microglia in the central nervous system, satellite glia in the dorsal root ganglia or peripheral immune cells in a mammal suffering from neuropathic pain consisting of the administration of an amount of senicapoc sufficient to achieve at least 50% inhibition of the potassium channel $K_{Ca}3.1$ on microglia in the central nervous system, satellite glia in the dorsal root ganglia or peripheral immune cells, wherein the inhibition of microglia $K_{Ca}3.1$ channels treats neuropathic pain.

2. The method of claim 1 wherein the administration of senicapoc comprises a dosage form selected from an oral tablet, an oral capsule, a powder for dissolution or suspension in a drinkable liquid, and an injectable dosage form.

* * * * *